United States Patent [19]

Johnson

[11] Patent Number: 4,767,602

[45] Date of Patent: Aug. 30, 1988

[54] APPARATUS FOR REDEPOSITING PARTICULATE MATTER

[75] Inventor: David L. Johnson, Syracuse, N.Y.

[73] Assignee: The Research Foundation of State University of New York, Albany, N.Y.

[21] Appl. No.: 592,701

[22] Filed: Mar. 23, 1984

[51] Int. Cl.$^4$ .............................................. C01N 33/48
[52] U.S. Cl. ..................................... 422/101; 422/99; 422/100; 422/102; 436/177
[58] Field of Search ...................... 422/58, 59, 60, 68, 422/101, 99, 100, 102; 436/174, 177; 250/440.1; 356/36, 38; 73/863.23, 863.24

[56] References Cited

U.S. PATENT DOCUMENTS

| | | | |
|---|---|---|---|
| 2,323,669 | 2/1960 | Poitras | 435/311 |
| 3,783,105 | 1/1974 | Moyer et al. | 422/58 |
| 3,825,410 | 7/1974 | Bagshawe | 422/101 |
| 3,847,552 | 11/1974 | Hobgood et al. | 422/56 |
| 4,180,383 | 12/1979 | Johnson | 422/101 |
| 4,304,805 | 12/1981 | O'Brien et al. | 422/101 |
| 4,493,815 | 1/1985 | Fernwood et al. | 436/177 |

*Primary Examiner*—Michael S. Marcus
*Attorney, Agent, or Firm*—Howard M. Ellis; Michael L. Dunn

[57] ABSTRACT

Virtual quantitative transfer of air and water borne particulates from a collection media to a more suitable media for individual particle micro-analytical procedures is performed with a redeposition spot sampler employing transfer fluids preferably in conjunction with ultrasonic vibration. Provides quantitative control over the particle loading per unit area of "new" filter media.

11 Claims, 1 Drawing Sheet

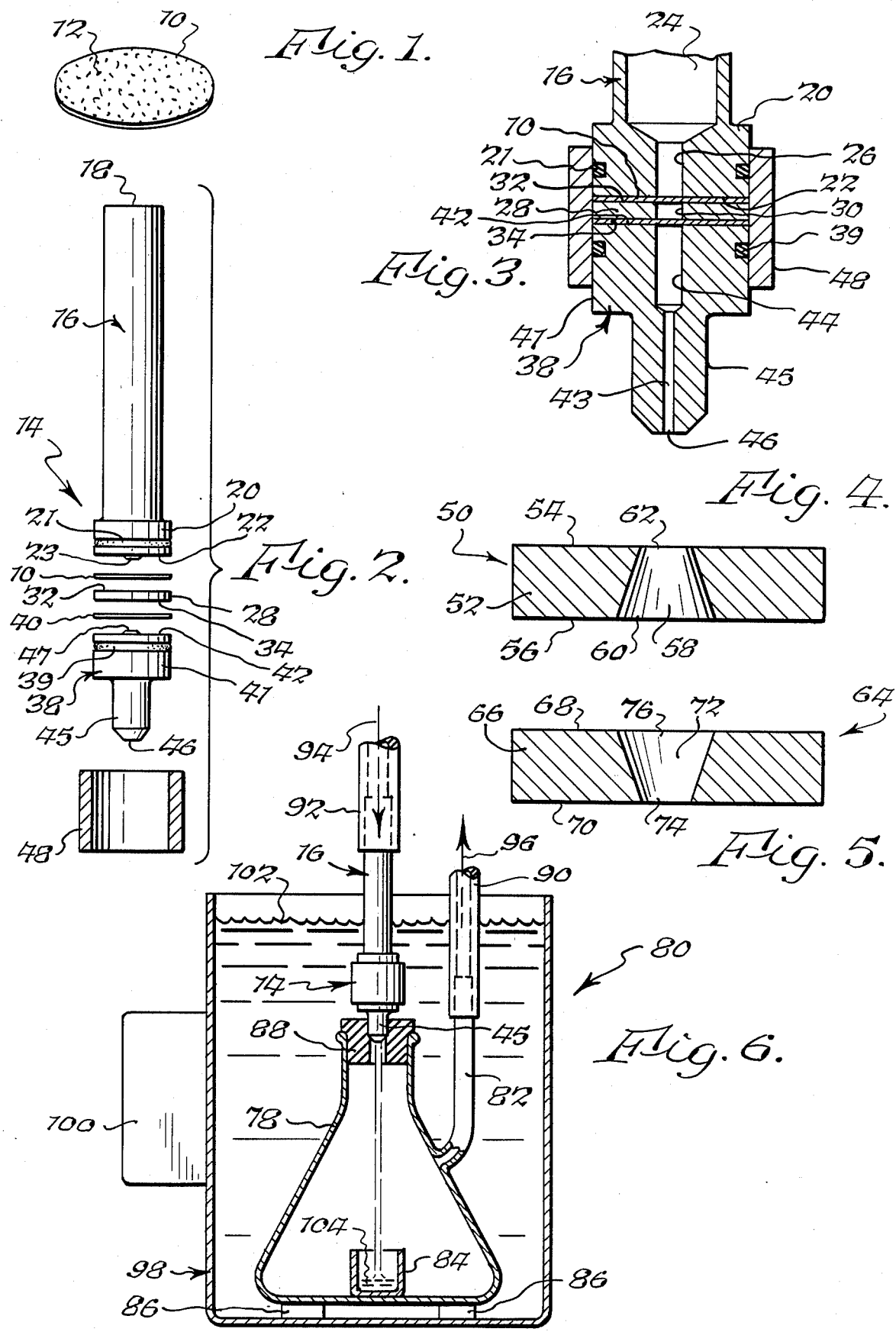

APPARATUS FOR REDEPOSITING PARTICULATE MATTER

BACKGROUND OF THE INVENTION

The present invention relates to the transfer of collected particulate matter. More specifically, this invention relates to a novel device and method for redeposition of particulate matter from one type of medium to another type of medium which is more suitable for use in connection with microscopic examination and analysis of individual particles.

Specimens of particulate matter present in air, water, biological systems and other sources are routinely collected for analysis. These specimens have been generally characterized by bulk chemical analysis which provides an average composition of a sample, but completely ignores information concerning individual particles within the heterogeniety of the sample.

Individual particle analyses have relied on sophisticated microscopic techniques, such as analytical light microscopy (ALM), scanning electron microscopy (SEM), laser microprobe mass analysis (LAMMA) and scanning transmission electron microscopy (STEM). However, such techniques have been employed only qualitatively for individual particle analysis. But with the recent advent of computer control of analytical processes coupled with image analysis individual particle characterization techniques can now be placed on a quantitative basis. That is, statistically significant populations of particles can be characterized over shorter time periods, e.g. 500–1000 features/hour. Accordingly, sample preparation for these types of analyses becomes more critical in developing accurate information and data.

Typically, samples of particulate matter are collected on glass fiber and cellulose filter medium. In the case of a sparsely loaded sample, particles can become intimately associated with the collection media's fiber matrix and are often deposited deep within the media. In the case of heavier loading of particles on collection media, there is a tendency of particle overlap occurring, and consequently, a lower resolution of individual particle analysis. In each of these techniques, individual particles should be redeposited onto a smooth, flat, chemically simple surface, e.g. polycarbonate membrane, and dispersed in such a manner that the individual particles of the specimen are analyzable.

Heretofore, particle transfer and redeposition mechanisms relied on three basic techniques: physical transfer by "wetted" needles; "vacuum cleaning" from the original filter and backflushing by solvents while treated with ultrasonic energy. Such methods have not been totally satisfactory for reasons that physical transfer removes only surface particles from the original membrane providing neither qualitative nor quantitative transfer. Vacuum cleaning methods, although more reliable than physical transfer, nevertheless are not quantitative.

Typically, backflushing in combination with ultrasonic agitation has involved the steps of initially placing a filter sample on aluminum foil backed with paperboard whereupon multiple disks are cut from the original sample for extraction of the particulates. Each disk is placed between perforated stainless steel screens, installed in a pressure filtration holder and immersed in a container of solvent, e.g. acetone, containing the probe tip of a sonic dismembrator. Filtered acetone is forced through the assembly and the direction of flow reversed. The solvent and particulate mixture are collected together in a separator container. The flushing would be repeated and reversed several times for each filter section. The mixture would then be conducted through a more suitable filter for individual particle analysis. As can be readily observed, this system fails to provide control of the area subjected to the redeposition process. That is, besides increasing the risk of physical contamination of the sample and loss of particles through multiple process steps, such methods employing the backflush approach failed to provide means whereby small known areas of original filter could be flushed so that the particles are redeposited on a known area of "new" substrate. Thus, the loading mass per unit area which is critical to efficient processing of individual particle analysis results was not appropriately taken into account. Too heavy a loading can impede accurate analysis of individual particulates due to particle overlap, whereas too light a loading detracts from time-efficient analysis. Accordingly, there is a need for an improved device and method for redepositing individual particles in preparation of samples for analysis, particularly on a micro scale.

The present invention provides a novel redeposition spot sampler device and method for substantially complete and potentially quantitative release and transfer of particulate matter from a collection medium to a more suitable medium for microscopy and individual particle analysis. That is, the immediate invention provides the means to quantitatively control in a uniform and homogeneous fashion the desired level of increase or decrease in particulate loading per unit area of "new" filter media, or in other words, the density or closeness of a population of reseated particles on a more favorable media for more accurate analysis. Although the device can be any size, it is especially well suited for micro scale analysis of individual particles permitting the use of only a small portion of the original medium while allowing preservation of the balance of the medium for other analytical procedures, e.g. bulk analysis.

In addition, this invention also provides convenient alternative means for redepositing particles relating, for instance, to fractional redeposition of a sample, either chemically or physically.

SUMMARY OF THE INVENTION

The present invention provides for a novel process for substantially complete removal and transfer of specimen particles from an area on a first substrate to a defined area on a second substrate. The process generally provides for first identifying for analysis an area on an original collection media containing a particle deposit. Media for collecting specimens of particulates ordinarily are unsuitable for most micro-analytical procedures, and therefore, must be transferred to a more suitable medium. The identified deposit of particle(s) on this first media is isolated from the remaining particle deposits preferably by mounting the entire collecting medium between first and second surfaces having corresponding apertures whereby the side of the media having the deposit is adjacent to the second surface. Only the specimen identified for redeposition is aligned with the apertures on each of the surfaces. The medium on which the specimen is to be transferred is mounted axially to the first medium between third and fourth surfaces, each of said surfaces having an aperture corresponding to the apertures in the first and second surfaces. An appropriate fluid is then conducted through each of the corresponding apertures beginning with the aperture in the first surface. The fluid passes first through the backside of the collection medium transferring the identified specimen onto an area of "new" medium at a density which is more conducive for individual particle analysis.

The particular fluid, combination of fluids or sequences of fluid addition and conditions under which the transfer of particles is carried out are those which are most favorable for the release of particles from the original medium and transfer to the new medium in order to achieve virtually complete or substantially quantitative transfer of particles.

The present invention also contemplates a novel redeposition device for substantially complete removal and transfer of particulate matter from collection substrates to substrates which are more suitable for use in processes for individual particle analyses. The device comprises a fluid reservoir having a fluid inlet and a base. The bottom, exterior portion of the reservoir base is equipped with a planar surface for seating the collection substrate containing the particulate matter. The base also includes an aperture which communicates with the fluid reservoir. The redeposition device includes a substrate support positioned axially to the reservoir base and is equipped with a planar surface for seating the new porous substrate for receiving the identified particulates removed from the collection substrate. The substrate support also has an aperture corresponding to the aperture in the reservoir base, which also serves as a fluid outlet for the device. A divider for separating the two substrates is disposed between the planar surfaces of the reservoir base and the substrate support, and includes an aperture corresponding to the apertures in each of said base and support members. Clamping means are employed for holding the fluid reservoir, substrate support and a substrate separator in longitudinal alignment without loss of fluid or particulates.

BRIEF DESCRIPTION OF THE DRAWINGS

For a further understanding of the invention, as well as the characterizing features, reference should now be made to the following detailed description taken thereof in conjunction with the accompanying drawings wherein:

FIG. 1 is a perspective view of an original filter media with particle deposits.

FIG. 2 is a side elevational view of the redeposition device with individual component parts spaced from one another.

FIG. 3 is a vertical sectional view of elements of the redeposition device assembled.

FIG. 4 is a sectional view of a particle dispersing separator.

FIG. 5 is a sectional view of a particle concentrating separator.

FIG. 6 is a vertical sectional view of a laboratory set-up including particle redeposition device installed in an ultrasonic cleaner bath.

DESCRIPTION OF PREFERRED EMBODIMENTS

Turning now to FIG. 1, there is provided a collection substrate 10 usually comprised of either a glass fiber, cellulose or other type of porous filter medium, which is generally unsatisfactory for use in state of the art analytical procedures, such as SEM, ALM, STEM, LAMMA, etc. This type of medium is frequently used in gathering specimens of particulates 12 for analysis, including airborne particulates, particulates in water, biological systems and other sources where, for instance, government regulatory agencies need to determine air and water quality compliance. Therefore, in order to aid in developing data on such collected particles means are provided herein for substantially quantitative redeposition of particles 12 from collection medium 10 to a medium more suitable for microscopy and individual particle analysis.

FIG. 2 provides a redeposition spot sampler 14 for removing and transferring particulates from collection medium 10 to a second medium 40, said device comprising a tubular member 16, a second medium support 38 positioned axially to the tubular member 16, a medium separator 28 disposed between the tubular member and the second medium support, and a ring member 48 for holding the tubular member, second medium support and medium separator in axial alignment. More specifically, the tubular member 16 includes a fluid inlet 18 at a first end which forms a central opening 24 (FIG. 3), said opening serving as a fluid conduit and reservoir for transfer fluids, i.e. solvents and gases used in removing particles from an identified spot on the collection medium and redepositing the particles onto the new or second medium 40.

Tubular member 16 is also equipped with a base 20 at a second end thereof, said base having an exterior, planar, optically flat first surface 22. An aperture 26 (FIG. 3) through base 20 usually of narrowed diameter extends from surface 22 to central opening 24. Optionally, but preferably, base 20 includes an outer seal in the form of O-ring 21 of conventional design fabricated from rubber elastomer material which aids in sealing the device against loss of fluid and particulates during redeposition.

As a further feature of the redeposition device, surface 22 of the base of tubular member 16 may include a rim 23 which is essentially a narrow lip surrounding the outer edge of aperture 26 forming a slight elevation on the surface. This optional feature provides greater pressure on the adjoining aperture in the medium separator as well as the collection medium thereby assuring particle transfers which are more closely quantitative.

The medium separator 28 positioned between first surface 22 of the base and second medium support 38 has opposing second and third planar surfaces 32 and 34 and a centrally positioned aperture 30 corresponding to aperture 26 in base 20 and aperture 44 (FIG. 3) of second medium support 38. The diameter of separator 28 generally corresponds to the diameter of base 20 and platform 41 of second medium support 38. In one embodiment, the first and second surfaces 22 and 32 provide close fitting, optically flat seating for collection substrate 10 minimizing the diffusion of transfer fluid between the planar surfaces assuring preservation of non-redeposited particles on the medium for future analysis. The side of the collection medium 10 with deposited particles 12 is in juxtaposition with the second planar surface 32. Surfaces 32 and 34 may, as in the case of surface 22, have a slightly elevated rim or lip (not shown) surrounding the outer edges of aperture 30 to even further limit the potential for lost transfer material.

The second medium support 38 which is positioned axially to tubular member 16 and medium separator 28 functions primarily as a platform and support for the second medium 40, and comprises a platform body 41 having a fourth planar surface 42 for seating the second medium. Support 38 also includes a stem 45 shown with a narrowed outside diameter and a narrowed aperture 43 communicating with aperture 44, the later aperture corresponding to the apertures in base 20 and medium separator 28. Aperture 44 and 43 extend from surface 42 through stem 45 providing an outlet 46 for transfer fluids. The platform body is also preferably equipped with an elastomeric O-ring 39 reducing the potential for loss of transfer materials during redeposition. Optionally, the fourth surface 42 can also have a slightly elevated rim or lip 47 (FIG. 2) surrounding the outer edge of aperture 44.

The second medium 40 which may be, for example, a smooth, flat membrane made of a polycarbonate type material, such as available from the Nuclepore Corporation and designed for SEM and LAMMA analyses is clamped between third and fourth surfaces 34 and 42. Other suitable transfer media for redeposition could include cellulose acetate type filters which can be used in ALM, since this type of media can be "cleared" or made optically transparent. Other media include, for example, filters fabricated from PTFE.

A retaining ring 48 which is an outer sleeve-like element fits around the periphery of base 20, separator 28 and platform body 41, including the collection (first) and transfer (second) media to assure proper alignment of all elements and tight, leak-proof joints. Use of a sleeve 48 is but one embodiment of appropriate means for holding the fluid reservoir, substrate support and separator in proper axial alignment. However, alternative means will be apparent to persons skilled in the art for holding the elements of the device together, including spring loaded clamps and the like.

It will be noted, in FIG. 3 apertures 26, 30 and 44 are of the same or substantially the same diameter. Under such circumstances, the density of redeposited particles on the spot of new filter medium will be the same because of the uniform cross-sectional configuration of the aperture sidewall of the separator. However, it may be desirable to adjust the mass loading per unit area of filter to an optimum level in which case alternative separators may be employed according to the present invention. That is, in some instances it may be desirable to either disperse the redeposited particles over a larger surface area, or alternatively, concentrate a sparce number of particles into a smaller defined area of a filter medium. FIG. 4 provides an embodiment of a modified separator 50 for dispersing an identified spot of particulates over a larger surface area. The separator body 52 includes planar surfaces 54 and 56 for intimate contact with the collection and transfer media 10 and 40. The aperture 58 is tapered so as to provide a frustoconical cross-sectional configuration with a wide base 60 and a narrower mouth 62.

FIG. 5 provides a third embodiment of a separator element 64 for redepositing and concentrating a sparsely populated area of particulates onto a controlled, smaller area on the transfer medium. Body 66 includes planar surfaces 68 and 70 on opposing sides of the separator. The separator orifice 72 is tapered so as to form a funnel shape with a narrowed base 74 and a widened mouth 76.

The redeposition device described herein may be fabricated from a wide range of suitable polymeric, ceramic and metallic materials, such as stainless steel, brass, glass and the like. Other suitable inert materials include polyolefins like polyethylene, polypropylene; polyesters including nylons, polycarbonate resins, as well as the fluorinated polymers like PTFE. Teflon ® based plastics and other fluorinated polyolefins are especially desirable because of their favorable chemical and physical properties, including inertness which permit easy cleaning even with strong mineral acids without adversely affecting their surface characteristics or dimensional stability of individual components of the device. Although use of gaskets are generally preferred to ensure against possible leakage, fluoropolymers do provide exceptionally smooth, flat surfaces and their machined and lapped surfaces seal well with thin, high tensil strength membrane filters. Thus, in some instances, the need for O-rings or gasket seals can be eliminated.

The apparatus described hereinabove has been illustrated with reference to miniaturized-type Spot laboratory redeposition devices specifically designed for SEM analyses, etc., utilizing, for example, 13 mm diameter membranes. It should be understood, however, the disclosed concepts are equally applicable to larger devices including larger collection media and greater volumes of particulate matter for transfer.

As indicated above, the invention also relates to a method for substantially complete removal providing a virtual quantitative transfer of particulates from an area on a first porous medium to a second porous medium. The method generally provides for a sequence of steps of first identifying an area on a side of the first medium containing a deposit of particles for analysis; isolating the identified area from the remaining particle deposits on the first medium by mounting the medium between the first and second planar surfaces with the side of the first medium having the particle deposits being mounted against the second planar surface with the identified particles aligned with their corresponding apertures. The second medium, i.e., transfer medium is mounted axially to the first medium between third and fourth planar surfaces having apertures corresponding to the apertures in the first and second surfaces. In order to effectuate the particle transfer, a fluid is then passed through each of the corresponding apertures beginning with the first planar surface. The conditions for optimizing the release and transfer of particles will be described in greater detail below.

FIG. 6 illustrates a set-up 80 for the redeposition of particulates utilizing the foregoing redeposition device 14. After identifying a deposit of particulates for analysis, the collection medium and transfer medium are mounted in redeposition device 14 following the previously described sequence of steps. The set-up 80 comprises a narrow neck glass container or flask 78 equipped with a side-arm outlet 82. A receptacle 84 is seated below the neck of container 78 for collecting transfer fluid, i.e. solvent and soluble particulates 104. A single hole stopper 88 affixed to stem 45 of the redeposition device seals the flask against loss of vacuum or pressure and entry of surrounding fluids. A connector 90 affixed over side arm 82 provides a lead to vacuum line 96. Alternatively, a connector 92 may be affixed to inlet 18 of the fluid reservoir 24 for applying pressure via line 94. Flask 78 is mounted at 86 inside the tank of a laboratory vibrator or cleaner 98 to agitate the particles. Vibrator/cleaner system 98 powered by motor 100 is filled with a liquid medium 102, usually water.

The redeposition process is initiated by conducting a transfer fluid contained in the reservoir 24, passing through the backside of the original collection medium flushing only the particles in alignment with the apertures previously described, redepositing the particles onto a suitable porous redeposition membrane/filter medium below. The transfer fluid may be comprised of a gas, such as air, nitrogen, etc., as well as a large variety of solvents, both polar and non-polar types, including water, alcohols, e.g. ethanol, methanol; acetone, chloroform, hexane and other well-known hydrocarbon solvents. Flushing is preferably carried out under vacuum. The transfer fluid 104 as an eluant collecting in receptacle 84 can be retained for analysis of compounds released during the redeposition process.

Although not required in every instance, in many cases the transfer process can be enhanced by exposing the particles to some form of agitation. Agitation/vibration may overcome the electrostatic attractive forces which cause particles to cling to the original collection medium, and in a physical sense can aid in moving deeply deposited particles through the tortuous pathways of the original filter medium. Thus, for redepositions which are potentially quantitative the process can be conveniently conducted by exposing particles, for example, to sounds having frequencies which are sufficient to assist in the transfer process, but without degradation of the particles. Generally, it has been found that frequencies in the ultrasonic range of at least 20,000 cycles/sec. provide satisfactory results. More specifically, soundwaves having frequencies of about 20,000 to about 40,000 cycles/sec. have been found most satisfactory.

The present invention also provides other analytical advantages. For example, multiple redeposition steps can be carried out with the present device on a given specimen by employing "fractional" redeposition methods. That is, multiple transfer steps may be used leading to chemical and/or physical fractionation by exposing an original spot sample to a sequence of extraction fluids in which a new transfer medium is used for each extraction step. For example, a first fluid, such as air can be employed to transfer larger, unbonded particles. The transfer medium is then replaced with a fresh membrane and a second extraction and redeposition can be carried out with water as the transfer fluid which will operate to flush smaller and/or charged particles owing to the greater transfer of ultrasonic vibrations to the particles.

A third fluid, such as hexane, could then be conducted through the original spot sample after replacing the second filter membrane which will operate to release particles bound by natural organic matter to the collection substrate.

The following specific example demonstrates the subject matter of the instant invention, however, it is to be understood that this example is for illustrative purposes only and does not purport to be wholly definitive as to conditions and scope.

EXAMPLE

A GHIA PTFE membrane is used for collecting the fine fraction of a dichotomous sample for individual particle analysis by Scanning Electron Microscopy with Automated Image Analysis and X-ray Energy Spectroscopy (SAX). Because large quantities of sulfur are present as individual particles on the membrane, SAX is often limited in characterization of the fine particles. Adjacent particle X-ray fluorescence interference may also cause incorrect chemical classification of a particle because the nonsulfur particles present show sulfur X-ray from their neighbors. In addition to the foregoing sulfur problem, the particles of interest are deposited at some depth within the membrane screening them from SAX characterization. It is also possible that some portions of the collection membrane per se will be characterized by SAX and counted as particles. These difficulties are obviated by quantitative and qualitative accurate redeposition of the particles from the original GHIA membrane to a 0.4 micrometer pore size polycarbonate membrane from Nuclepore Corp., using the redeposition device illustrated in FIG. 2 fabricated from PTFE and the set-up generally as shown in FIG. 6.

The particles are redeposited from a known area of the original GHIA membrane to a known area of the new polycarbonate membrane. The dimensions of each of the areas need not be equal as long as they are known; in that way the quantitative transfer of mass per unit area is preserved.

The bottom medium support of the redeposition device for the new filter is first affixed to a Quartz, Vycor or other clean material fluid collection container using a standard taper ground glass joint. A 13 mm diameter, Aerosol grade, 0.4 micrometer pore size Nuclepore membrane is then placed on the bottom medium support with Teflon forceps which had been previously cleaned in 6N Ultrex nitric acid and rinsed in "particle free" water. The connecting sleeve previously washed in acid and rinsed in particle free water is inserted over the O-ring of the bottom medium support. The medium separator is then placed in the connecting sleeve and over the membrane. A section of the original membrane is selected for redeposition. A 13 mm diameter circle is carefully removed with a surgical steel cutting ring. Once again, using Teflon forceps, this circle of original medium is then placed upside-down so that the side of the membrane containing the particles to be transferred is in contact with the medium separator within the connecting sleeve. The upper portion of the redeposition device consisting of the fluid reservoir is then placed on the back-side of the exposed original collection medium and the entire apparatus clamped in place. The fluid inlet of the reservoir may be temporarily covered to avoid possible contamination.

The device is then inserted into the fluid bath of a laboratory ultrasonic cleaner filled with water. Alternatively, Bromoform or other high specific gravity liquid may be employed in the ultrasonic cleaner if particularly "resistant particles" are to be redeposited. The ultrasonic cleaner is activated and allowed to run for a 30 second pretreatment period during which a vacuum is applied to the solvent collection container with a pressure drop of 15 inches of mercury.

Subsequently, the reservoir cover is removed and 4 ml of Reagent/Spectro-Grade acetone added to the reservoir, assuming an original and redeposited membrane area of 4 mm². At this rate of refiltration, one ml of solvent for every square mm of filter surface is appropriate. The redeposition process is completed in 3 to 8 minutes.

Upon completion, the fluid reservoir of the redeposition device is removed and the original filter medium archived for future reference and the medium separator plate removed. The "new" membrane is then mounted on a graphite stub and prepared for SAX. The redeposition solvent can then be subjected to GC, GC/MS, HPLC, IC, INAA, or other appropriate analytical chemical technique in order to carry out a bulk analysis for important soluble constituents of the original sample, now available as a result of the redeposition process.

While the invention has been described in conjunction with a specific example thereof, this is illustrative only. Accordingly, many alternatives, modifications and variations will be apparent to those skilled in the art in light of the foregoing descriptions, and it is therefore intended to embrace all such alternatives, modifications and variations as to fall within the spirit and broad scope of the appended claims.

What is claimed is:

1. A redeposition spot sampler comprising:
   (a) A fluid reservoir having a fluid inlet, a central opening and a base portion, said base portion comprising an exterior surface for seating a first porous substrate with particle deposits and an aperture communicating with said central opening, the cross-sectional area of the aperture being smaller than the cross-sectional area of the base portion for providing fluid contact only with that portion of the substrate in alignment with said aperture and preserving the particle deposits in that portion of the substrate not aligned with said aperture,
   (b) substrate support means positioned axially to the base portion of the reservoir, said support means being equipped with a surface for seating a second porous substrate for receiving particles from the first substrate, said support means including an aperture axially aligned with the aperture in the base portion of the reservoir forming a fluid outlet for the device,
   (c) substrate separator means for separating the first and second porous substrates disposed between the exterior surface of the base portion of the reservoir and the seating surface of the substrate support, said substrate separator means having aperture means axially aligned with the apertures in the base portion of the reservoir and substrate support means for allowing free passage of particles from the first substrate to the second substrate, and
   (d) means for holding the fluid reservoir, substrate support means and substrate separator means in axial alignment without loss of fluid or particles.

2. The device of claim 1 wherein the substrate separator means has opposing surfaces with elevated rims on said surfaces surrounding the peripheral edges of the aperture means.

3. The device of claim 1 wherein the exterior surface of the base portion of the reservoir and the seating surface of the substrate support have elevated rims at the peripheral edges of their respective apertures.

4. The device of claim 3 wherein the holding means is a concentric sleeve circumscribing the base portion of the reservoir, substrate support means and substrate separator means.

5. The device of claim 3 wherein the apertures in the base portion of the reservoir, substrate support means and substrate separator means are substantially the same diameter.

6. The device of claim 3 wherein the aperture in the substrate separator means is substantially funnel shaped.

7. A device for removal and transfer of a spot of particulate matter from a first medium to a second medium, which comprises:
   (a) a tubular member having a fluid inlet at a first end, a central opening and a base portion at a second end, said base portion having an exterior, substantially planar surface for seating the first medium, an aperture communicating with the central opening and an elevated rim on said exterior surface at the peripheral edge of the aperture,
   (b) medium support means positioned axially to the base portion of the tubular member, said support means having a substantially planar surface for seating the second medium and an aperture axially aligned with the aperture in the base portion of the tubular member forming a fluid outlet for the device, the medium support surface having an elevated rim at the peripheral edge of the medium support aperture,
   (c) a medium separator having substantially planar surfaces for positioning between the base portion of the tubular member and medium support means surface, said separator having an aperture axially aligned with the apertures in the base portion of the tubular member and medium support means allowing free passage of particulate matter from the first medium to the second medium, and
   (d) means for holding the tubular member, medium support means and medium separator in axial alignment without loss of fluid or particulate matter.

8. The device of claim 7 wherein the apertures have substantially equivalent diameters.

9. The device of claim 7 wherein the aperture in the medium separator is substantially funnel shaped.

10. The device of claim 7 wherein the holding means is in the form of an outer sleeve member.

11. The device of claim 10 wherein the fluid outlet in the medium support means is in the form of an axially aligned stem.

* * * * *